United States Patent [19]

Barnett et al.

[11] 4,307,248

[45] Dec. 22, 1981

[54] PROCESS FOR HYDROGENATING ORGANIC COMPOUNDS BY USE OF NON-FERROUS GROUP VIII ALUMINUM COPRECIPITATED CATALYSTS

[75] Inventors: Allan E. Barnett; Albert P. Halluin, both of Westfield, N.J.

[73] Assignee: Exxon Research & Engineering Co., Florham Park, N.J.

[21] Appl. No.: 210,775

[22] Filed: Nov. 28, 1980

Related U.S. Application Data

[63] Continuation-in-part of Ser. No. 91,836, Nov. 6, 1979, Pat. No. 4,273,939.

[51] Int. Cl.$^3$ .................... C07C 5/10; C07C 29/14; C07C 85/12; C11C 3/12
[52] U.S. Cl. .................. 564/358; 252/455 R; 252/466 J; 252/466 PT; 260/27 R; 260/409; 564/375; 564/385; 564/490; 564/493; 568/814; 568/881; 568/882; 568/883; 585/267; 585/276; 585/277; 585/269; 585/270
[58] Field of Search .............. 564/358, 375, 385, 490, 564/493; 585/270, 269, 277, 267; 568/881, 883

[56] References Cited

U.S. PATENT DOCUMENTS

| | | | |
|---|---|---|---|
| 2,009,948 | 7/1935 | Schmidt et al. | 568/881 X |
| 2,391,283 | 12/1945 | Weber et al. | 585/270 |
| 2,673,189 | 3/1954 | Reynolds et al. | 585/270 X |
| 3,320,182 | 5/1967 | Taylor et al. | 252/466 |
| 3,371,050 | 2/1968 | Taylor et al. | 252/459 |
| 3,385,670 | 5/1968 | Hook et al. | 23/212 |
| 3,432,443 | 3/1969 | Davies et al. | 252/459 |
| 3,544,485 | 12/1970 | Taira et al. | 568/881 X |
| 3,547,830 | 12/1970 | Shropshire | 252/432 |
| 3,627,790 | 12/1971 | Stiles | 585/270 X |
| 3,697,445 | 10/1972 | Carter | 252/452 |
| 3,859,370 | 1/1975 | Carter et al. | 260/638 B |
| 3,868,332 | 2/1975 | Carter et al. | 252/452 |
| 3,926,584 | 12/1975 | Adsetts | 48/214 |
| 3,932,534 | 1/1976 | Fukunaga et al. | 585/270 X |
| 3,932,547 | 1/1976 | Mertzweiller et al. | 585/270 X |
| 3,954,601 | 5/1976 | Cosyns et al. | 585/277 X |
| 4,088,603 | 5/1978 | Carter et al. | 252/454 |
| 4,090,980 | 5/1978 | Carter et al. | 252/454 |
| 4,113,658 | 9/1978 | Geus | 252/454 |

FOREIGN PATENT DOCUMENTS

| | | | |
|---|---|---|---|
| 1340366 | 9/1963 | France | 568/881 |
| 39-13055 | 7/1964 | Japan | 564/493 |
| 49-47304 | 5/1974 | Japan | 564/493 |
| 1183637 | 3/1970 | United Kingdom | 568/881 |
| 319582 | 12/1971 | U.S.S.R. | 585/269 |
| 403658 | 3/1974 | U.S.S.R. | 585/269 |

OTHER PUBLICATIONS

Yates et al., "J.A.C.S.", vol. 86, pp. 2996–3000, (1964).

*Primary Examiner*—John Doll
*Attorney, Agent, or Firm*—Henry E. Naylor

[57] ABSTRACT

Supported coprecipitated catalysts comprised of one or more metals of Group VIII, one or more metals of Group IIA, and aluminum are used for hydrogenating hydrogenatable organic compounds. The catalysts are produced by preparing, under agitation; an aqueous mixture containing ions of Group VIII, Group IIA, and aluminum, as well as solid porous particles to form a coprecipitate of the metal ions and aluminum ions with the solid porous support particles; heating the aqueous reaction mixture; and adding precipitating agent to precipitate the metal ions and aluminum ions onto the solid support.

20 Claims, No Drawings

PROCESS FOR HYDROGENATING ORGANIC COMPOUNDS BY USE OF NON-FERROUS GROUP VIII ALUMINUM COPRECIPITATED CATALYSTS

CROSS-REFERENCE TO RELATED APPLICATIONS

This application is a Continuation-in-Part application of U.S. Ser. No. 91,836, filed Nov. 6, 1979, now U.S. Pat. No. 4,273,939.

BACKGROUND OF THE INVENTION

1. Field of the Invention

The present invention relates to supported coprecipitated metal-aluminum catalyst wherein the metal is selected from the group consisting of the non-ferrous metals of Group VIII of the Periodic Table of Elements. These catalysts are useful in hydrogenating organic compounds.

2. Description of the Prior Art

The catalytic reduction of organic compounds in the presence of one or more metals of Group VIII of the Periodic Table of the Elements, particularly nickel and cobalt as well as nickel-cobalt or nickel-cobalt-copper catalysts is known. For example, U.S. Pat. No. 3,320,182 teaches the preparation of a coprecipitated catalyst by slowly adding ammonium bicarbonate to an aqueous solution containing nickel nitrate and aluminum nitrate at elevated temperatures. These catalysts are taught to have a reduced nickel surface area of 20–30 m²/g of catalyst. The coprecipitation of nickel salts from an aqueous solution seeded with porous silica or porous alumina is taught in U.S. Pat. No. 3,371,050. This '050 patent discloses a precipitation process wherein nickel nitrate is precipitated from an aqueous solution containing either porous silica or gamma alumina particles. Example 10 of the '050 patent discloses the coprecipitation of nickel and silicate ions from an aqueous solution seeded with porous silica. Example 11 of the '050 patent teaches that the addition of copper salts to the aqueous solution will promote the nickel catalyst in Town Gas production. The nickel surface area of such catalysts is disclosed as ranging from 40–60 m²/g of catalyst.

D. J. C. Yates, W. F. Taylor and J. H. Sinfelt (J. Am. Chem. Soc., 86, 2996 [1964]) described a chemisorption technique and its utility in correlating nickel particle size (and/or nickel surface area) with catalytic activity. In FIG. 3 of their publication, there is shown that a direct relation exists between reduced nickel surface area (m²/g of catalyst) and initial reaction rate for ethane catalytically converted into methane (as mmols $C_2H_6$ converted per hour per gram of catalyst). It follows, then, that methods which increase the nickel surface area of a nickel catalyst (other factors such as nickel content remaining constant) is a desirable feature, leading to a catalyst of improved catalytic activity. Patentees of U.S. Pat. Nos. 3,697,445; 3,859,370 and 3,868,332 also appreciated that by achieving a higher degree of dispersion of nickel in the catalyst results in a more active catalyst and indeed they obtain a fairly high degree of dispersion by their coprecipitation techniques wherein nickel cations were gradually precipitated from an aqueous solution in the presence of silicate anion and solid porous particles to obtain dispersion greater than 70 m²/g of reduced nickel metal per gram of catalyst. Belgium Pat. No. 841,812 teaches that the addition of copper ions during the precipitation step provides a catalyst that can be reduced at temperatures of approximately 200° C. U.S. Pat. No. 4,088,603 discloses an improved method of activating the coprecipitated nickel-copper-silica catalysts.

A number of patents have disclosed cobalt, cobalt-nickel and cobalt-nickel-copper catalysts, e.g., U.S. Pat. Nos. 3,166,491; 3,385,670; 3,432,443; 3,547,830; 3,650,713; 3,661,798; 3,945,944; 4,014,933 and 4,026,823; and British Pat. Nos. 1,000,828; 1,000,829; 1,095,996; 1,095,997 and 1,182,829. None of these patents, however, disclose coprecipitation of one or more Group VIII metal ions and aluminum ions in the presence of solid porous support particles.

Recently, U.S. Pat. No. 4,113,658 has disclosed a method for the controlled dispersion of metal on a coprecipitated catalyst. For example, nickel nitrate and support particles are coprecipitated by gradually increasing the alkalinity of the aqueous reaction mixture.

SUMMARY OF THE INVENTION

In accordance with the present invention, a supported coprecipitated metal-aluminum catalyst is prepared wherein the metal portion of the catalyst is one or more metals selected from the group consisting of the non-ferrous metals of Group VIII of the Periodic Table of the Elements. The catalysts of the present invention are characterized as having a B.E.T. total surface area ranging from about 150 to about 350 m²/g. The total amount of the non-ferrous Group VIII metal in the catalyst ranges from about 25 wt. % to about 70 wt. % based on the total weight of the calcined and reduced catalyst.

The catalysts of the present invention are prepared by:

(a) preparing a heated aqueous reaction mixture comprised of (i) at least one water-soluble metal salt of a metal selected from the group consisting of non-ferrous metals of Group VIII of the Periodic Table of Elements; (ii) a water soluble aluminum salt; and (iii) solid porous support particles; and (b) adding a precipitating agent to the heated reaction mixture to coprecipitate the metal ions and aluminum ions with the solid porous support particles. The heated aqueous reaction mixture may be prepared by either mixing hot solutions of the salts and the solid support particles or by mixing the reaction mixture ingredients under ambient temperature conditions, and thereafter heating the reaction mixture to elevated temperatures, preferably at temperatures greater than 60° C., and more preferably at temperatures ranging from 75° C., to the boiling point of the reaction mixture at atmospheric pressure. Preferably, the reaction mixture is vigorously agitated or mixed and maintained at elevated temperatures for a brief period of time, e.g., one to five hours. The heating step may be conducted at ambient pressures or elevated pressures (i.e., to reduce evaporation). Following precipitation the catalyst can then be washed, dried, and calcined. If desired, the calcined catalyst can be activated by reduction.

The catalyst may include up to about 10 wt. %, based on the total weight of the catalyst, of various additives such as metals selected from Groups IB and IIA of the Periodic Table of the Elements. These additives may be included in the catalyst by coprecipitation of their salts with the other metal salts or by impregnation, etc., coprecipitation is preferred.

The total B.E.T. surface area of the catalyst will preferably range from about 150 to about 350 m$^2$/g of catalyst, more preferably from about 225 m$^2$/g to about 335 m$^2$/g. When nickel is the metal used to prepare the catalyst, the reduced nickel surface area of the calcined catalyst will be greater than about 50 m$^2$/g, preferably greater than about 55 m$^2$/g and may be as high as 100 m$^2$/g or more. Generally the reduced nickel surface area of the calcined catalyst will range from about 55 to about 75 m$^2$/g, and more often from about 60 to about 75 m$^2$/g.

The catalysts of the present invention are useful for hydrogenating hydrogenatable organic compounds such as aromatic compounds, aldehydes, alcohols, edible fats and oils, aromatics in white oil base stock, nitro compounds, nitriles, and unsaturated and substituted hydrocarbons. The catalysts can also be used in an oxo process for producing alcohols, aldehydes, etc., as well as being used as a pollutant scavenger for such pollutants as nitrogen oxides.

DETAILED DESCRIPTION OF THE INVENTION

The catalysts of the present invention are produced by preparing a heated aqueous reaction mixture containing aluminum anions, solid porous particles and metal ions selected from the group consisting of the non-ferrous metals of Group VIII of the Periodic Table of the Elements and precipitating the aluminum anions and metal ions with the solid porous particles. All reference to the Periodic Table of the Elements herein refers to the Periodic Table of the Elements illustrated in the inside covers of the 55th Edition of the Handbook of Chemistry and Physics published by CRC Press (1974). Typical non-ferrous Group VIII metals useful in the practice of the invention include nickel, cobalt, platinum, iridium, palladium, rhenium, rhodium and ruthenium. Nickel and cobalt are the preferred non-ferrous Group VIII metals, and nickel is the most preferred.

The coprecipitated catalysts of the present invention can be prepared by various techniques. For example, all the components of the reaction mixture (e.g., the metal salts and solid porous carrier particles) may be placed in a suitable reaction vessel under acidic conditions and thereafter the hydroxyl ion concentration is increased while heating and agitating the slurry. In connection with this technique, reference is made to U.S. Pat. No. 4,113,658, the disclosure of which is incorporated herein by reference. Another technique involves dissolving the metal salts (e.g., nickel nitrate and aluminum nitrate) in water under agitation and at elevated temperatures, preferably ranging from 60° C. up to the solution's boiling point at atmospheric pressure. Higher temperatures may be employed provided that the solution is under pressure. The solid porous particles are then added to this agitated and heated reaction mixture. Generally, the dissolved metal ions in the reaction mixture will be kept below about 0.6 mols/liter. This dilution of the dissolved metal ions is one preferred means for obtaining high catalytic activity. Preferably, a precipitating agent is added to the heated reaction mixture to aid in the coprecipitation of the non-ferrous Group VIII metal with the aluminum ions and porous support particles.

During catalyst preparation, water may be added to the reaction mixture to maintain a nearly constant volume so that water loss by evaporation is continually replaced. The aqueous reaction mixture is preferably kept at elevated temperatures, e.g., from about 60° C. up to about the boiling point of the solution (at atmospheric pressure) for a period of one to five hours. Heating at a temperature below the boiling point of the solution, i.e., 60°–99° C., may be employed to minimize evaporation. The reaction mixture is then filtered and the resulting product is washed, preferably several times repeatedly with boiling water, to remove alkali metals and other impurities. (Generally the washings will be four or more times.) The catalyst is then dried at temperatures ranging from 90°–200° C., for one to five hours and calcined from an oxygen source, e.g., an oxygen-containing gas such as air to a temperature ranging from about 300°–450° C., for a period of about 2–8 hours, preferably about 3–5 hours. The finished catalyst can then be reduced or charged directly (or subsequent to shaping or extruding such as in the form of tablets or pellets) into the reaction vessel, without activation, and activated in the reaction vessel with a gaseous reductant, usually flowing hydrogen. Alternatively, the catalyst may be prereduced and passivated (stabilized) prior to charging into the reactor.

As stated previously, it is preferred that in preparing the catalyst of this invention, the coprecipitation of the catalyst is made from dilute solutions, i.e., the solution should have a metal concentration no greater than about 1.0 mol/liter and an aluminum nitrate concentration no greater than about 0.4 mols/liter. The most preferred solution used in preparing the catalyst has no more than about 0.75 mols/liter of metal ions, more preferably less than about 0.6 mols/liter and about 0.26 mols/liter of aluminum ions, e.g., aluminum nitrate. Such dilute solutions insure high metal surface area. This is contrasted with a more concentrated precipitation in which the solution contains up to twice as much solute. The mole ratio of metal to aluminum employed ranges from about 0.3:1 to about 2.5:1 in the calcined and reduced catalyst.

In the case of the aluminum porous alumina based catalysts about 30 to 90 wt. % of the total alumina content of the activated catalyst is derived from precipitated aluminum ions when the solid porous particles are comprised of alumina. Preferably, however, 50 to 70 wt. % of the total alumina content is derived from the aluminum ions when the solid porous particles are comprised of alumina.

The remaining steps in preparing and activating the catalyst are identical to those described above.

In a preferred aspect of the present invention, the catalyst is formed by coprecipitating, from an aqueous solution, aluminum ions and one or more metals selected from the group consisting of nickel or cobalt onto a solid porous particulate support, preferably solid porous silica and/or alumina, more preferably solid porous alumina.

When cobalt is the metal selected for the use herein, its source may be any of the following non-limiting examples: cobaltous nitrate, cobaltous chloride and cobaltous bromide.

When the selected metal is nickel, its source may include the non-limiting group selected from nickel nitrate, nickel chloride and nickel bromide.

Non-limiting examples of sources of aluminum ions suitable for use herein include aluminum nitrate, aluminum sulfate, aluminum chloride. Preferably the source of the aluminum ions is aluminum nitrate.

Other sources of metal ions as well as aluminum ions may be utilized and may be determined by one having ordinary skill in the art by either routine experimentation or general knowledge in the art. For example, the salts of the metals used herein are the water-soluble salts such as nitrates, halides, formates or oxalates.

Non-limiting examples of solid porous particles suitable for use herein include alumina, kieselguhr, infusorial earth, diatomaceous earth, siliceous earth and silica. Preferred is alumina particles, more preferred is eta and gamma alumina particles, and most preferred is gamma alumina particles. The concentration of the solid porous particles can be expressed as percent of total alumina or silica in the catalyst and may range from about 10 wt. % to about 70 wt. %, preferably from about 30 wt. % to about 50 wt. %.

It is preferred, especially in the case of nickel and/or cobalt, that the coprecipitation of these ions with aluminum ions in aqueous solution containing the solid porous particles be completed by the addition of a water soluble alkaline precipitating agent. The alkaline ammonium precipitants such as ammonium bicarbonate or ammonia are most suitable for minimizing the amount of alkali metal residue which has to be removed by washing to avoid poisoning action on the finished catalyst. In some instances, the potassium precipitants may be used where the potassium acts as a promoter rather than a poison. Sodium carbonate is another example of a suitable water-soluble alkaline precipitating compound. Various organic alkaline materials such as urea, and primary and secondary amines may be used to complete the precipitation. However, a preferred precipitating agent is ammonium bicarbonate.

The precipitated catalyst is preferably washed to remove impurities, particularly sodium. If it is desired to remove the trace levels of sodium in the catalyst, one may wash the filter cake with a washing liquor comprising a mixture of water and a small amount, i.e., about 100 ppm of a filtering aid such as sodium or potassium carbonate or nitrate or 200 ppm of ammonium carbonate. In this connection, reference is made to U.S. Pat. No. 4,105,591, the disclosure of which is incorporated herein by reference.

After the washing, drying and calcining is completed, the catalyst must be reduced in order to activate it. Reduction is carried out in the presence of a reducing gas, preferably hydrogen. The reducing gas is passed over the catalyst at ambient temperature at a rate of about 5 liters/hr/gm to about 30 liters/hr/gm and then the temperature is raised to a range of from about 75° C. to about 450° C., preferably from about 195° C. to about 400° C.

The reduction (activation) may be carried out after the catalyst has been loaded into the reaction vessel where the hydrogenation will be carried out, which may be either batch or continuous. The nature of the reactor will be obvious to one skilled in the art. The activation procedure of U.S. Pat. No. 4,088,603 may be used with the catalyst of the present invention.

The activated catalyst is sensitive to deactivation and may not be stored in the presence of oxygen at ordinary temperatures without first being passivated. The passivation step may consist of purging the reactor at a temperature greater than about 150° C. with an inert gas, preferably nitrogen, cooling to ambient temperature and then passing the inert gas over the catalyst while an air bleed is introduced into the inert gas so as to have approximately 1-2 mol percent oxygen present. This procedure will passivate the catalyst by putting a surface oxide coating on it. Preferably, the catalyst will be passivated by the process of U.S. Pat. No. 4,090,980, the disclosure of which is incorporated herein by reference.

The B.E.T. total surface area of the catalyst of the present invention will generally range from about 150 to about 350 m$^2$/g, preferably from about 225 m$^2$/g to about 325 m$^2$/g. The method for measuring the total catalyst surface area known as the B.E.T. method is described in Emmett, P. H., *Advances in Catalysis*, I. 65, (1948). Also, the catalyst preferably contains about 0.1 wt. % or less sodium based on the total weight of the catalyst.

Where nickel is chosen as the metal herein, the resulting catalyst is capable of having a nickel surface area ranging from about 55 to 100 m$^2$/g as determined by hydrogen chemisorption after reduction at 400° C., unless otherwise specified, in the manner described by Yates, Taylor and Sinfelt in *J. Am. Chem. Soc.*, 86, 2996 (1964), the disclosure of which is incorporated herein by reference. Also, the catalyst preferably contains about 0.1 wt. % or less of sodium and preferably from about 25 wt. % to about 50 wt. % nickel based on the total weight of the catalyst.

Where cobalt is chosen as the metal herein, the resulting catalyst is capable of having a cobalt surface area ranging from about 5 to about 20 m$^2$/g as determined by hydrogen chemisorption (discussed above) after reduction at 400° C. unless otherwise specified. Also, the catalyst preferably contains about 0.1 wt. % or less sodium and preferably from about 25 wt. % to about 60 wt. % of cobalt wherein all weight percents are based on the total weight of the catalyst.

The catalysts of the instant invention are useful in hydrogenating hydrogenatable organic compounds. In this connection, the catalysts of the instant invention may be used to hydrogenate aromatic containing compounds as typified by the hydrogenation of benzene to cyclohexane, the hydrogenation of aldehydes, both saturated and unsaturated to the alcohols as in the well-known oxo process, the hydrogenation of the double bonds in edible fats and oils as well as other olefins both straight and branched chain, the hydrogenation of aromatics in white oil base stock to produce high-grade white oil, the hydrogenation of nitro compounds to amines and the hydrogenation of nitriles to amines. Indeed, olefins as used herein signify unsaturated compounds having at least one multiple bond and contemplates polyunsaturated compounds as well.

The conditions for the hydrogenation reactions have been discussed very widely and are well known to those skilled in the art; broadly the following conditions may be utilized: temperatures ranging from about 25° C. to 300° C., preferably from 75° C. to 250° C.; pressures ranging from 1 atmosphere to 800 atmospheres, preferably from 1 atmosphere to 50 atmospheres; feed rates of from 0.2 to 100 volumes per hour per volume of catalyst and hydrogen addition of from 500 to 10,000 standard cubic feet per barrel (SCF/B) of feed may be used.

In the case of the oxo process, i.e., the addition of carbon monoxide and hydrogen to alkene to produce alcohols, aldehydes and other oxygenated organic compounds, one would typically employ conditions such that the temperatures would range from about 70° C. to 175° C. and use a hydrocarbon mole ratio of 0.5 to 10 and a pressure of 100 to 1000 psig. The alkenes used in such a process would typically contain 2 to 20 carbon atoms. The product of such a carbonylation process generally consists of aldehydes, acetals, unsaturated oxygenated materials and the like which require hydrofinishing in a second or further hydrogenation stage. It is to the treatment of the aldehyde product, in particular, that the present invention applies. Hydrogenation conditions in this further reaction stage follow those generally employed in the first stage.

Another useful improved hydrogenation is the conversion of aromatics in white spirits to yield high quality solvents. The upgrading of white spirits by the process of the instant invention is an improvement in the treatment of such materials.

Still another useful improved hydrogenation of the invention is the conversion of olefins in paraffin solvents such as denonenizer bottoms and deoctenizer overheads.

Two especially useful hydrogenation processes included within the scope of the invention include the hydrogenation of aromatics such as benzene to cyclohexane and the production of amines from nitro compounds and nitriles. For example, the invention is useful in converting $C_{12}$ to $C_{24}$ nitriles to the corresponding fatty acid amines. Also, aromatic nitro compounds may be converted to amines, e.g., nitrobenzene to aniline or the conversion of aromatic amines to cycloaliphatic amines, e.g., aniline to cyclohexane amine.

The following examples serve to more fully describe the manner of making and using the above-described invention, as well as to set forth the best modes contemplated for carrying out various aspects of the invention. It is understood that these examples in no way serve to limit the true scope of this invention, but rather, are presented for illustrative purposes.

EXAMPLE 1

Catalyst A was prepared as follows: 62.9 g of Ni($NO_3$)$_2$.6$H_2O$ and 33.1 g Al($NO_3$)$_3$.6$H_2O$ was dissolved in 560 ml of distilled water. The solution was heated to about 80° C. (but below the boiling point of the reaction mixture) and 2.8 g of solid porous particles of gamma alumina was added. The slurry had an acidic pH of 4. With rapid stirring, 52.4 g of the $NH_4HCO_3$ precipitating agent was added as fast as foaming would allow. The reaction mixture was maintained at the elevated temperature for 3 hours. The coprecipitated catalyst was filtered and washed by reslurrying 3 times with 2 liters of hot (>80° C.) distilled water. The resulting filter-cake was dried overnight at 110° C. and calcined for 3 hours at 400° C., the catalyst was reduced for 16 hours in hydrogen at 400° C. and had a calculated nickel content of 63.5 wt. % based on the total weight of the reduced catalyst. The resulting catalyst was also found to have a B.E.T. surface area of 240 m$^2$/g and reduced nickel surface area of 63.2 m$^2$/g. This catalyst was then used to hydrogenate benzene to cyclohexane, the results of which are shown in Table I.

COMPARATIVE EXAMPLE

Catalyst B was prepared as follows: 112 g of Ni($NO_3$)$_2$.6$H_2O$ was dissolved in 500 ml of distilled water, then 38 g of $Na_2SiO_3$.9$H_2O$ was dissolved in another 500 ml of water and 5 g of acid washed kieselguhr was slurried in the second solution. The second solution with kieselguhr slurried therein was stirred vigorously while the first solution containing the nickel salt was added to a uniform rate over a 20-minute period. This mixture was then heated to the boiling point of the mixture (at atmospheric pressure) and 80 g of $NH_4HCO_3$ was added to a uniform rate over a 20-minute period. The mixture was kept at the boiling point of the reaction mixture of 3 hours while stirring continued. It was then filtered and washed 5 times with boiling water, each wash consisting of 500 ml of distilled water. The filter cake was then dried at 120° C. and calcined in air for 4 hours at 400° C. The reduced nickel surface area was determined by hydrogen chemisorption, after reduction at 400° C., to be 65 m$^2$/g and it has a B.E.T. total surface area of 292 m$^2$/g. This catalyst was used to hydrogenate benzene to cyclohexane the results of which are shown in Table I.

TABLE I
CATALYTIC CONVERSION OF BENZENE TO CYCLOHEXANE[a]

| Minutes on Stream | Benzene Conversion % | |
|---|---|---|
| | Catalyst A | Catalyst B |
| 30 | 95 | 63.1 |
| 60 | 90 | 61.8 |
| 90 | 79 | 61.1 |
| 120 | 76.2 | 57.4 |
| 150 | 75.4 | — |
| 180 | 74.6 | 54.1 |
| 210 | 73.1 | 58.5 |
| 240 | 74.1 | 57.7 |

[a]Reaction Conditions: Pressure: 1 atmosphere; Temperature: 78° C.; Feed: 90% n-hexane, 10% benzene; feed rate: 20 cc/hr; $H_2$ rate: 20.4 1/hr; catalyst charge: 0.25 gm (catalyst reduced 16 hr. at 400° C.)

The above table illustrates that the nickel-aluminate catalyst of the present invention has a higher activity for hydrogenating benzene than a nickel-silicate catalyst of the prior art.

EXAMPLE 2

Catalyst C was prepared according to the procedure of Example 1 above except kieselguhr was substituted for gamma alumina as the solid porous support and 36 gm of sodium carbonate was used as the precipitating agent. This catalyst was also used to hydrogenate benzene to cyclohexane. This catalyst had a B.E.T. surface area of 177 m$^2$/g. The results are set forth in Table II.

EXAMPLE 3

Catalysts D and E were prepared according to Example 1 except that 3.99 g of Cu($NO_3$)$_2$.3$H_2O$ were dissolved in the distilled water along with the nickel nitrate and aluminum nitrate and 69.9 g of $NH_4HCO_3$ was used as the precipitating agent. In Catalyst E, 2.8 g of kieselguhr was substituted for the alumina as the solid porous support. Both of these catalysts were used to hydrogenate benzene to cyclohexane. The results are set forth in Table II.

EXAMPLE 4

Catalysts F and G were prepared according to Example 1 above except 56.66 g of Ni($NO_3$)$_2$.6$H_2O$, 33.1 g Al($NO_3$)$_3$.6$H_2O$, and 6.27 g of Co($NO_3$)$_2$.6$H_2O$, was dissolved in 560 ml of distilled water, 69.9 g $NH_4HCO_3$ was used as the precipitating agent, 2.8 g gamma alumina was the solid porous support for Catalyst F and 2.8 g of kieselguhr for Catalyst G. Both catalysts were also used to hydrogenate benzene to cyclohexane and the results are set forth in Table II.

EXAMPLE 5

Catalyst H and I were prepared according to Example 1 above except 56.6 g Ni($NO_3$)$_2$.6$H_2O$, 33.1 g Al($NO_3$)$_3$.6$H_2O$, 6.27 g Co($NO_3$)$_2$.6$H_2O$ and 3.99 g Cu($NO_3$)$_2$.3$H_2O$ were dissolved in 560 ml of distilled water. 69.9 g $NH_4HCO_3$ was used as the precipitating agent.

2.8 g of gamma alumina was the porous support for Catalyst H and 2.8 g kieselguhr was the porous support for Catalyst I. Both catalysts were used to hydrogenate benzene to cyclohexane. The results are set forth in Table II.

COMPARATIVE EXAMPLE

For the purposes of comparison an iron containing catalyst was prepared in the following manner: 91.2 gm of $Fe(NO_3)_3.9H_2O$ was dissolved in 500 ml of distilled water. To this solution there was added 2.8 gm of kieselguhr followed by the addition under conditions of vigorous mixing 200 ml of an aqueous solution containing 21.26 gm of $Na_2SiO_3.9H_2O)$. Mixing of this comingled solution was continued and followed by heating to about 80° C. The coprecipitation was completed by the addition of 67.2 gm of ammonium bicarbonate. The mixture was mixed for an additional 30 minutes after the last addition, and diluted to 4 liters with water, washed by decantation 2 times with 4 liter washes, filtered and dried at 120° C. The catalyst was calcined for 3 hours at 400° C. The catalyst had an argon B.E.T. total surface area after evacuation at 260° C. of 256 $m^2/g$. After overnight reduction at 400° C., the catalyst had a metal surface determined by hydrogen chemisorption to be less than one $m^2/g$ catalyst, and an argon B.E.T. surface area of only 132 $m^2/g$ of catalyst.

An attempt was made to convert benzene to cyclohexane using the iron catalyst prepared above. The reaction conditions were as follows: Pressure 1 atm; Temperature: 76°-77° C.; Feed: 90% N-hexane, 10% benzene; Feed Rate: 20 cc/hr; $H_2$ Rate: 20.4 liters/hour; Catalyst Charge: 0.25 gms of catalyst which had been reduced 16 hours at 400° C. Samples of the product were taken at 15 minutes, 30 minutes and 60 minutes and there was no sign of benzene conversion in any of these samples. The temperature was raised to 112° C. and the product was sampled to find no conversion of benzene to cyclohexane.

The above tests demonstrate that the non-noble metal silica coprecipitated compositions, i.e., nickel, cobalt and iron are not equivalent in their hydrogenation catalytic properties. The iron containing composite prepared by the process of U.S. Pat. No. 3,697,445 had substantially no detectable catalytic activity with respect to converting benzene to cyclohexane, whereas nickel and cobalt catalysts coprecipitated with silicate ions in the presence of silica particles have good hydrogenation catalytic activity.

EXAMPLE 6

Catalyst J was prepared by dissolving 62.9 g $Ni(NO_3)_3.6H_2O$ (0.216 moles), 3.99 g $Cu(NO_3)_2.3H_2O$ (0.017 moles) and $Al(NO_3)_3.9H_2O$ (0.167 moles) in 560 ml of agitated distilled water. The agitating mixture was heated to >80° C. (but below the boiling point of the mixture). 18.5 g $NH_4HCO_3$, precipitating agent, was added to the heated mixture to obtain turbidity, then 2.8 g gamma $Al_2O_3$ (available from Engelhardt) was added to the mixture. Additional $NH_4HCO_3$ was added to the mixture so that the total amount used was 69.9 g or 2.2 moles per mole of metal in the mixture. The mixture was maintained at >80° C. and mixing was continued for 2 hours after the final addition of precipitating agent. The resulting coprecipitate was filtered and washed twice by reslurrying with 2 liters of distilled water. The washed catalyst was placed in an oven to dry at 110° C. (30.35 g recovered). The dried catalyst was then placed in a furnace and calcined for 3 hours at 400° C. (22.6 g recovered). A sample of the catalyst was reduced overnight at 400° C. and analyzed to have a $H_2$ surface area (by chemisorption technique) of 23.1 $m^2/g$ and a B.E.T. total surface area of 206 $m^2/g$. The remainder of the catalyst was then reduced overnight at a temperature of 200° C. then tested for its ability to convert benzene to cyclohexane. The results of this test are shown in Table III below.

A similar catalyst preparation was made, identified as Catalyst K, using the same procedure, materials and concentrations described for Catalyst J except that kieselguhr was used in place of the $Al_2O_3$ seed. The catalyst after being reduced overnight at 400° C. was found to have a $H_2$ surface area (by chemisorption technique) of 32.3 $m^2/g$. The catalyst was then tested for its catalyst hydrogenation ability and the results shown in Table III.

TABLE III

CATALYTIC CONVERSION OF BENZENE TO CYCLOHEXANE[a]

| Minutes on Stream | (Ni/Cu/Al gamma alumina) Catalyst J | (Ni/Cu/Al kieselguhr) Catalyst K |
|---|---|---|
| 15 | 50 | 43.3 |
| 30 | 41.5 | 38.4 |
| 60 | 35.3 | 37.4 |
| 90 | 50.0 | — |
| 120 | 52.8 | — |
| 150 | 50.4 | — |
| 180 | 55.0 | — |
| 210 | 53.9 | — |
| 240 | 52.4 | — |

[a]Reaction Conditions: pressure: 1 atmosphere; temperature: 78° C.; feed: 90% n-hexane, 10% benzene; feed rate: 20 cc/hr; $H_2$ rate: 20.4 1/hr; catalyst charge: 0.25 g.

TABLE II

CATALYTIC CONVERSION OF BENZENE TO CYCLOHEXANE[a]

| Minutes on Stream | (Ni/Al/kieselguhr) Catalyst C | (Ni/Al/Cu/gamma alumina) Catalyst D | (Ni/Al/Cu/kieselguhr) Catalyst E | (Ni/Co/Al/gamma alumina) Catalyst F | (Ni/Co/Al/kieselguhr) Catalyst G | (Ni/Co/Al/Cu/gamma alumina) Catalyst H | (Ni/Co/Al/Cu/kieselguhr) Catalyst I |
|---|---|---|---|---|---|---|---|
| 60 | 91.4 | 35.3[b] | 43.3 | 65.9 | 48.3 | — | 45.0 |
| 120 | 83.7 | 52.8 | 37.3 | 58.4 | 44.6 | — | 38.4 |
| 180 | 74.0 | 55.0 | — | 53.7 | 42.4 | — | 32.4 |
| 240 | 73.2 | 52.4 | — | 51.1 | 41.25 | 43.0 | 33.0 |

[a]Reaction Conditions: pressure: 1 atmosphere; temperature: 78° C.; feed: 90% n-hexane, 10% benzene; feed rate: 20 cc/hr; $H_2$ rate: 20.4 1/hr; catalyst charge: 0.25 g. (catalyst reduced 16 hours at 400° C.).
[b]Same as (a) above but at a temperature at 72° C.

This table illustrates that the nickel-aluminate catalyst of the present invention, even when supported on kieselguhr has a higher activity for hydrogenating benzene than similar catalyst containing one or more additional metals.

This table again illustrates that the nickel-aluminate catalyst unexpectedly has a relatively high hydrogenation activity.

EXAMPLE 7

Catalyst L was prepared by dissolving 56.66 g of $Ni(NO_3)_2.6H_2O$, 6.27 g $Co(NO_3)_2.6H_2O$, 33.1 g $Al(NO_3)_3.9H_2O$ and $Cu(NO_3)_2.6H_2O$ in 560 ml of agitated distilled water. The agitating mixture was heated to $>80°$ C. (but below the boiling point of the mixture). 18.5 g $NH_4HCO_3$, precipitating agent, was added to the heated mixture to obtain turbidity, then 2.8 g gamma $Al_2O_3$ (available from Engelhardt) was added to the mixture. Additional $NH_4HCO_3$ was added to the mixture so that the total amount of $NH_4HCO_3$ employed was 69.9 g. The mixture was maintained at $>80°$ C. and mixing was continued for 2 hours after the final addition of precipitating agent. The resulting coprecipitate was filtered and washed twice by reslurrying with 2 liters of distilled water. The washed catalyst was placed in an oven to dry at 110° C. The dried catalyst was then placed in a furnace and calcined for 3 hours at 400° C. A sample of the catalyst was reduced overnight at 400° C. and analyzed to have a $H_2$ surface area (by chemisorption) of 41.5 $m^2/g$. The remaining catalyst was then reduced overnight at 200° C. and tested for its ability to hydrogenate benzene to cyclohexane using the reaction conditions specified in Tables I, II and III herein. After 15 minutes at 80° C., 24.3% of the benzene was converted to cyclohexane and after 30 minutes at 78° C., 17.5% of the benzene was converted to cyclohexane. Although this catalyst system demonstrated a relatively low hydrogenation activity for benzene, it was interesting to note that this hydrogenating activity was present even when the catalyst was activated at 200° C. rather than the conventional 400° C.

The following examples illustrate the superior hydrogenation performance of the nickel/aluminum catalysts of the present invention which have been coprecipitated in the presence of solid porous particles, when compared with nickel/aluminum catalysts which have been coprecipitated in the absence of such particles. Thus, the importance of employing solid porous particles is herein illustrated.

Comparative Example

Catalyst M was prepared by dissolving 74.1 g of $Ni(NO_3)_2.6H_2O$ and 37 g of $Al(NO_3)_3.9H_2O$ in 186 ml of distilled water. 75.3 g of $Na_2CO_3$ (precipitating agent) was also dissolved in 200 ml of distilled water. Both solutions were heated above 90° C. (but below the boiling point of the solution with rapid stirring. The mixture was maintained at that temperature, with rapid stirring for 30 minutes. The resulting coprecipitated catalyst was filtered and washed until the pH of the filtrate had fallen below 8. The filtrate was dried at 110° C. and calcined for 6 hours at 450° C. A sample of the calcined catalyst was reduced in hydrogen at 400° C. for 16 hours and was found to have a hydrogen area of 40.2 $m^2/g$ (equivalent to reduced nickel surface area). The catalyst was also found to have a B.E.T. surface area of 126 $m^2/g$. Another sample of the catalyst was used to hydrogenate benzene to cyclohexane. The results are set forth in Table IV below.

EXAMPLE 8

Catalyst N was prepared according to the procedure used for preparing Catalyst M except 74.1 g of $Ni(NO_3)_2.6H_2O$, 23.5 g of $Al(NO_3)_3.9H_2O$, 50 g of $Na_2CO_3$, and 1.8 g of 2.8 g gamma $Al_2O_3$ were employed. After reducing a sample of the catalyst in hydrogen for 16 hours at 400° C., it was used to hydrogenate benzene to cyclohexane. The results are set forth in Table IV below.

It was previously disclosed in this specification that the catalysts of the instant invention may contain up to about 10 wt. %, based on the total weight of the catalyst, of various additives such as metals selected from Groups IB and IIA of the Periodic Table of the Elements. A preferred group of such additives include the salts of the metals of Group IIA of the Periodic Table of the Elements. Such metals include magnesium, barium, strontium, calcium, beryllium and radium. Most preferred are magnesium and barium.

The following example illustrates the superior performance of those catalysts of the present invention which include Group IIA metals.

Comparative Example

Catalyst O was prepared according to the procedure used for the preparation of catalyst M, except 74.1 g of $Ni(NO_3)_2.6H_2O$, 34.6 g of $Al(NO_3)_3.9H_2O$, 57 g of $Na_2CO_3$, and 1.9 g of $Mg(NO_3)_2.6H_2O$ were employed. After reducing a sample of the catalyst in hydrogen for 16 hours at 400° C. it was used to convert benzene to cyclohexane. The results are shown in Table IV below.

EXAMPLE 9

Catalyst P was prepared according to the procedure used for preparing catalyst M except 74.1 g of $Ni(NO_3)_2.6H_2O$, 21.3 g of $Al(NO_3)_3.9H_2O$, 50 g of $Na_2CO_3$, 1.9 g of $Mg(NO_3)_2.6H_2O$, and 1.8 g of gamma $Al_2O_3$ were employed. After reducing a sample of the catalyst in hydrogen for 16 hours, it was used to convert benzene to cyclohexane. The results are shown in Table IV below.

TABLE IV

CATALYTIC CONVERSION OF BENZENE TO CYCLOHEXANE[a]

| Minutes on Stream | Benzene Conversion % | | | |
|---|---|---|---|---|
| | Catalyst M | Catalyst N | Catalyst O | Catalyst P |
| 15 | | 87.4 | 64.6 | 96.1 |
| 30 | 45.5 | 79.5 | 60.1 | 93.0 |
| 60 | 40.1 | 70.9 | 56.3 | 85.4 |
| 120 | 36.2 | 63.4 | 52.7 | 78.3 |
| 180 | 34.4 | 60.0 | 51.4 | 76.2 |
| 240 | 33.1 | 58.6 | 49.4 | 72.4 |

[a]Reaction Conditions: Pressure: 1 atmosphere; Temperature: 78° C.; Feed: 90% n-hexane, 10% benzene; Feed Rate: 20 cc/hr; $H_2$ Rate: 20.4 l/hr; Catalyst Charge: 0.25gm (catalyst reduced 16 hr. at 400° C. with $H_2$).

As previously discussed, up to about 10 wt. %, based on the total weight of the catalyst after calcination and reduction, of one or more metals selected from Group IIA of the Periodic Table of the Elements may be employed. Preferably about 0.05 to 10 wt. %, more preferably about 0.1 to 8 wt. %, and most preferably about 0.5 to 6 wt. % of one or more Group IIA metals are employed in the instantly claimed catalyst. It is also preferred that the precipitating agent be sodium carbonate when the Group IIA metal is employed. This is so because a precipitating agent such as ammonium bicarbonate will interact with the Group IIA metal thereby causing incomplete precipitation of the metal ions of the instantly claimed catalyst.

What is claimed is:

1. A process for hydrogenating organic compounds which comprises contacting at least one hydrogenatable organic compound with hydrogen in the presence of a supported coprecipitated catalysts comprised of:
   (a) one or more metals selected from the nonferrous metals of Group VIII of the Periodic Table of the Elements,
   (b) aluminum,
   (c) porous particles, and
   (d) one or more metals selected from Group IIA of the Periodic Table of the Elements, said catalyst being characterized as having a B.E.T. total surface area ranging from about 150 to about 350 m$^2$/g, wherein the total amount of Group VIII metal in the catalyst ranges from about 25 wt. % to about 70 wt. %, and the total amount of the Group IIA metal in the catalyst is up to about 10 wt. %, both amounts of metals being based on the total weight of the catalyst after calcination and reduction, and wherein said catalyst has been prepared by coprecipitating the aluminum ions, the Group IIA and Group VIII metal ions with the solid porous particles.

2. The process of claim 1 wherein the catalyst contains about 0.1 to 8 wt. % of one or more Group IIA metals.

3. The process of claim 2 wherein the Group IIA metal is magnesium or barium.

4. The process of claim 1 wherein the catalyst contains about 0.1 wt. % or less of sodium based on the total weight of the active catalyst.

5. The process of claim 1 wherein the solid porous particles are selected from the group consisting of kieselguhr, infusorial earth, diatomaceous earth, siliceous earth, silica and alumina.

6. The process of claim 5 wherein the solid porous particles are alumina.

7. The process of claim 6 wherein the amount of solid porous particles ranges from about 10 wt. % to about 70 wt. % based on the total amount of alumina in the catalyst.

8. The process of claim 7 wherein the amount of the porous solid particles ranges from 30 wt. % to about 50 wt. % based on the total amount of alumina in the catalyst.

9. The process of claim 1 wherein the metal is selected from the group consisting of nickel, cobalt and mixtures of nickel and cobalt.

10. The process of claim 8 wherein the metal is selected from the group consisting of nickel, cobalt and mixtures of nickel and cobalt.

11. The process of claim 1 wherein said hydrogenation is conducted at a temperature ranging from about 75° C. to about 300° C., at a pressure ranging from about 1 atmosphere to about 12,000 psig; at a feed rate ranging from about 0.2 to about 100 V/Hr/V and at a H$_2$ rate ranging from about 500 to about 10,000 SCF/B.

12. The process of claim 10 wherein said hydrogenation is conducted at a temperature ranging from about 75° C. to about 300° C., at a pressure ranging from about 1 atmosphere to about 12,000 psig, at a feed rate ranging from about 0.2 to about 100 V/Hr/V and at a H$_2$ rate ranging from about 500 to about 10,000 SCF/B.

13. The process of claim 1 wherein at least one of the organic compounds is benzene.

14. The process of claim 12 wherein at least one of the organic compounds is benzene.

15. The process of claim 1 wherein at least one of the organic compounds is aldehyde.

16. The process of claim 12 wherein at least one of the organic compounds is an aldehyde.

17. The process of claim 1 wherein at least one of the organic compounds is a nitrile.

18. The process of claim 12 wherein at least one of the organic compounds is a nitrile.

19. The process of claim 1 wherein at least one of the organic compounds is an olefin.

20. The process of claim 12 wherein at least one of the organic compounds is an olefin.

* * * * *